United States Patent [19]

Gerry

[11] Patent Number: 4,901,851
[45] Date of Patent: Feb. 20, 1990

[54] CLEANING PACKAGE

[76] Inventor: Martincic Gerry, Ljubo Mrakovcic 10, 51417 Moscenicka Draga, Yugoslavia

[21] Appl. No.: 330,169

[22] Filed: Mar. 29, 1988

[51] Int. Cl.$^4$ ............................................. B65D 69/00
[52] U.S. Cl. ..................................... 206/223; 206/210; 206/484; 206/812
[58] Field of Search ............... 206/38, 209, 210, 223, 206/484, 568, 570, 572, 581, 812; 15/244.3, 244.4

[56] References Cited

U.S. PATENT DOCUMENTS

| 2,194,364 | 3/1940 | Minor | 15/244.4 |
|---|---|---|---|
| 2,835,911 | 5/1958 | Mahmarian | 15/244.4 |
| 3,005,219 | 10/1961 | Miller | |
| 3,005,543 | 10/1961 | Morse | 206/484 |
| 3,150,049 | 9/1964 | Emory | 206/484 |
| 3,240,326 | 3/1966 | Miller | 206/484 |
| 3,258,011 | 6/1966 | Goodman | |
| 3,629,896 | 12/1971 | Sirnee | |
| 3,857,133 | 12/1974 | Linenfelser | |
| 4,232,128 | 11/1980 | Michel et al. | 15/244.4 |
| 4,343,061 | 8/1982 | Hanazono | |
| 4,437,567 | 3/1984 | Jeng | 206/210 |
| 4,696,393 | 9/1987 | Laipply | 206/210 |
| 4,749,080 | 6/1988 | Toohey | 206/210 |
| 4,769,267 | 9/1988 | Hoyt | 15/244.4 |

FOREIGN PATENT DOCUMENTS

| 2717128 | 11/1978 | Fed. Rep. of Germany | 206/210 |
|---|---|---|---|
| 2724305 | 12/1978 | Fed. Rep. of Germany | 206/210 |

Primary Examiner—David T. Fidei
Attorney, Agent, or Firm—Jerry T. Kearns

[57] ABSTRACT

A cleaning implement for feminine hygiene uses includes first and second sponges sealed within an easily portable water proof outer package. A first packet within the outer package is formed from a water proof material and contains a first sponge having a front absorbent surface with a dense array of spaced wave form ridges and a back surface formed by a thin soft flexible plastic film. The first sponge is treated with sterilized water and a mild soap for preliminary cleaning. A second packet in the outer package is formed from a water proof material and encloses a second sponge treated with sterilized water and a subtle fragrance for final cleaning purposes. The first and second sponges may be formed from synthetic materials or from absorbent paper.

3 Claims, 3 Drawing Sheets

CLEANING PACKAGE

BACKGROUND OF THE INVENTION

1. Field of the Invention

The present invention relates to cleaning implements, and more particularly pertains to a new and improved cleaning implement for feminine hygiene uses. Modern home and public rest rooms are no longer equipped with a bidet for facilitating feminine hygiene. In order to compensate, the present invention provides a conveniently portable cleaning implement which includes first and second sponges treated with sterilized water and mild cleaning agents to facilitate feminine hygiene. Many women are sensitive or allergic to standard soaps and treated municipal tap water supplies. In order to overcome these problems, the present invention provides first and second sponges treated with sterilized water and mild cleaning agents and fragrances for use by women away from their homes.

2. Description of the Prior Art

Various types of cleaning implements are known in the prior art. A typical example of such a cleaning implement is to be found in U.S. Pat. No. 3,005,219, which issued to C. Miller on Oct. 24, 1961. This patent discloses a reversible polyurethane cleaning pad having two adhesively secured layers with a first absorbent layer and a second open mesh scrubbing layer. U.S. Pat. No. 3,258,011, which issued to H. Goodman on June 28, 1966, discloses a sponge seat for rectal treatment which dispenses liquid in response to a patient's body weight. The device is formed as a cylindrical disc having a peripheral water impermeable covering. U.S. Pat. No. 3,629,896, which issued to M. Sirnee on Dec. 28, 1971, discloses a cleaning implement including a sponge having a recessed peripheral edge with a cover having an edge portion secured in the recess and wrapped around the sponge to form a scrubbing layer. U.S. Pat. No. 3,857,133, which issued to C. Linenfelser on Dec. 31, 1974, discloses a dual purpose sponge formed from a polyurethane foam having an abrasive surface thermally bonded to a sponge foam body. U.S. Pat. No. 4,343,061, which issued to Y. Hanazono on Aug. 10, 1982, discloses a body washing implement formed from an annular sponge deformed to produce two close loop portions having a generally FIG. 8 shaped implement having a covering cloth of relatively coarse meshed fabric.

While the above mentioned devices are directed to cleaning implements, none of these devices disclose a portable disposable feminine hygiene cleaning system which includes first and second sponges treated with sterilized water, a mild soap and fragrance in a water proof portable package. Additionally, none of the aforesaid devices disclose a sponge having a front surface including an array of wave form ridges and a back surface covered by a water proof soft flexible plastic film. Inasmuch as the art is relatively crowded with respect to these various types of cleaning implements, it can be appreciated that there is a continuing need for and interest in improvements to such cleaning implements, and in this respect, the present invention addresses this need and interest.

SUMMARY OF THE INVENTION

In view of the foregoing disadvantages inherent in the known types of cleaning implements now present in the prior art, the present invention provides an improved cleaning implement. As such, the general purpose of the present invention, which will be described subsequently in greater detail, is to provide a new and improved cleaning implement which has all the advantages of the prior art cleaning implements and none of the disadvantages.

To attain this, a representative embodiment of the concepts of the present invention is illustrated in the drawings and makes use of a cleaning implement for feminine hygiene uses which includes first and second sponges sealed within an easily portable water proof outer package. A first packet within the outer package is formed from a water proof material and contains a first sponge having a front absorbent surface with a dense array of spaced wave form ridges and a back surface formed by a thin soft flexible plastic film. The first sponge is treated with sterilized water and a mild soap for preliminary cleaning. A second packet in the outer package is formed from a water proof material and encloses a second sponge treated with sterilized water and a subtle fragrance for final cleaning purposes. The first and second sponges may be formed from synthetic materials or from absorbent paper.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto. In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting. As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new and improved cleaning implement which has all the advantages of the prior art cleaning implements and none of the disadvantages.

It is another object of the present invention to provide a new and improved cleaning implement which may be easily and efficiently manufactured and marketed.

It is a further object of the present invention to provide a new and improved cleaning implement which is of a durable and reliable construction.

An even further object of the present invention is to provide a new and improved cleaning implement which is susceptible of a low cost of manufacture with regard to both materials and labor, and which accordingly is then susceptible of low prices of sale to the consuming public, thereby making such cleaning implements economically available to the buying public.

Still yet another object of the present invention is to provide a new and improved cleaning implement which provides in the apparatuses and methods of the prior art some of the advantages thereof, while simultaneously overcoming some of the disadvantages normally associated therewith.

Still another object of the present invention is to provide a new and improved cleaning implement for facilitating feminine hygiene.

Yet another object of the present invention is to provide a new and improved cleaning implement which includes first and second sponges in a portable disposable water proof package for facilitating feminine hygiene.

Even still another object of the present invention is to provide a new and improved cleaning implement for facilitating feminine hygiene which includes sterile water and mild soap and fragrance treated sponges in a disposable integral package.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
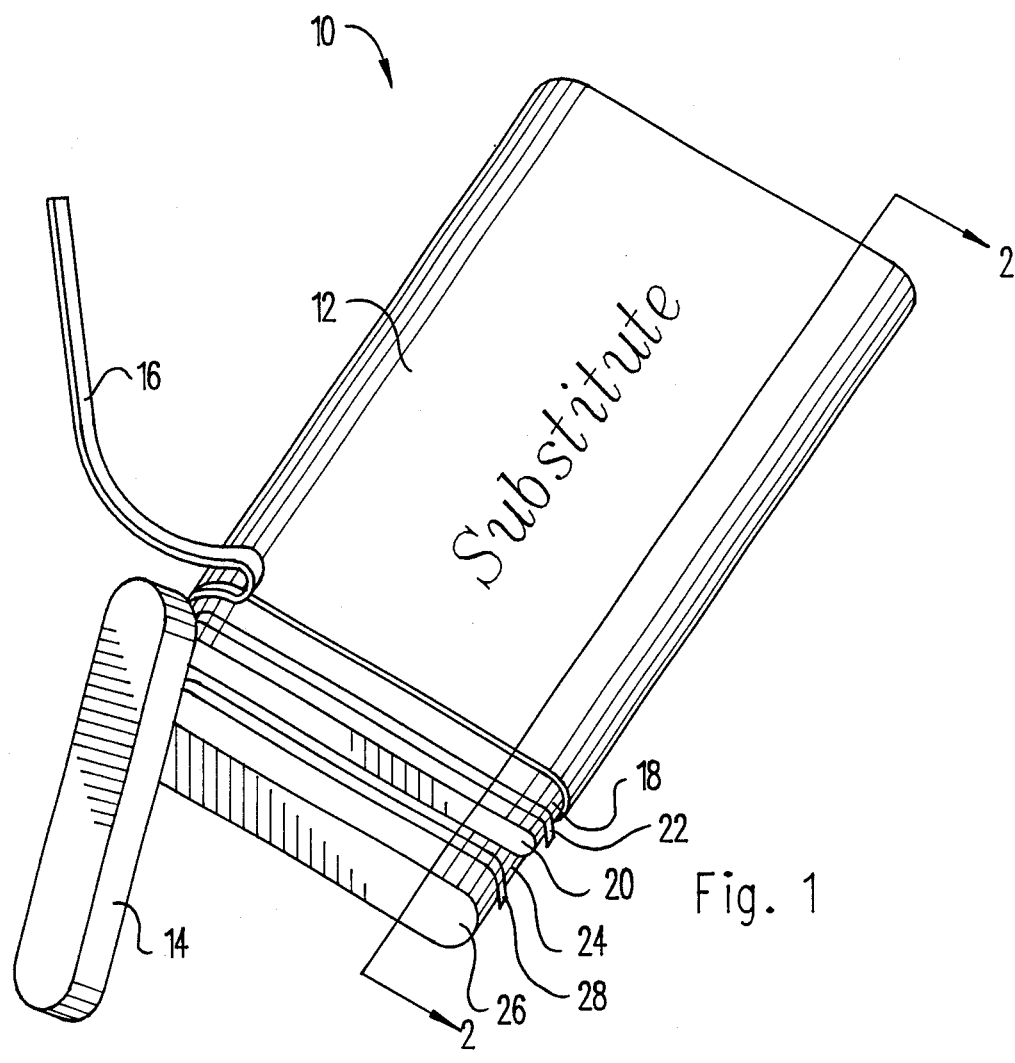
FIG. 1 is a perspective view of the cleaning implement of the present invention.

With reference now to the drawings, and in particular to FIG. 1 thereof, a new and improved cleaning implement embodying the principles and concepts of the present invention and generally designated by the reference numeral 10 will be described.

More specifically, it will be noted that the first embodiment 10 of the invention includes an outer package 12 preferably formed from a flexible water proof plastic or foil film. A removable cap portion 14 may be secured to the package 12 by a removable tear strip 16 to facilitate convenient opening of the disposable package 12. A first packet 18 and a second packet 24 are received in overlying relation within the outer package 12. The first packet 18 has a cap portion 20 secured by a peel-off strip 22 and the packet 24 has a similar cap 26 secured by a peel-off strip 28. Thus, the contents of the packets 24 and 18 are isolated from each other within the outer packet 12.

Figure 2:
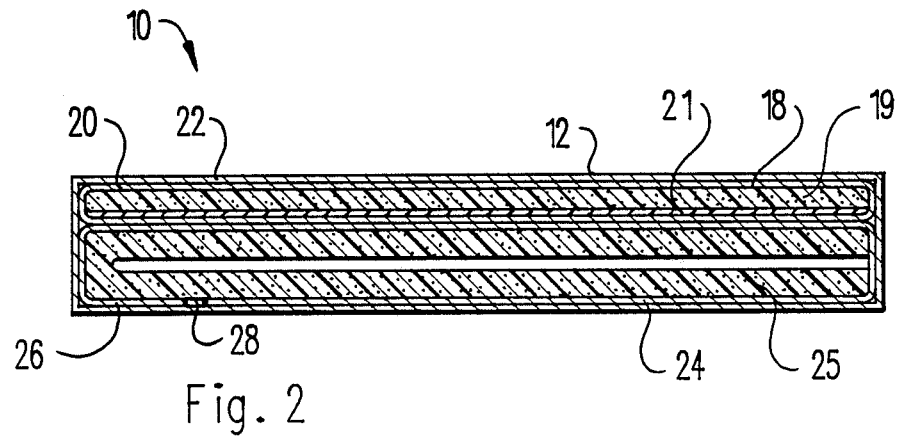
FIG. 2 is a cross sectional view, taken along line 2—2 of FIG. 1.

FIG. 2 is a cross sectional view, which illustrates the contents of the first packet 18 and the second packet 24. The first packet 18 contains a first sponge 19 which is preferably treated with sterilized water and a mild soap. The back surface of the sponge 19 is covered by a thin soft water proof flexible plastic film 21 which maintains an individual's hand out of contact with the opposite absorbent surface of the sponge 19. The second packet 24 encloses a folded sponge 25 which is preferably treated with sterilized water and an optional mild fragrance or freshening agent. The sponges 19 and 25 may be formed from a synthetic polyurethane foam material or from a soft absorbent paper.

Figure 3:
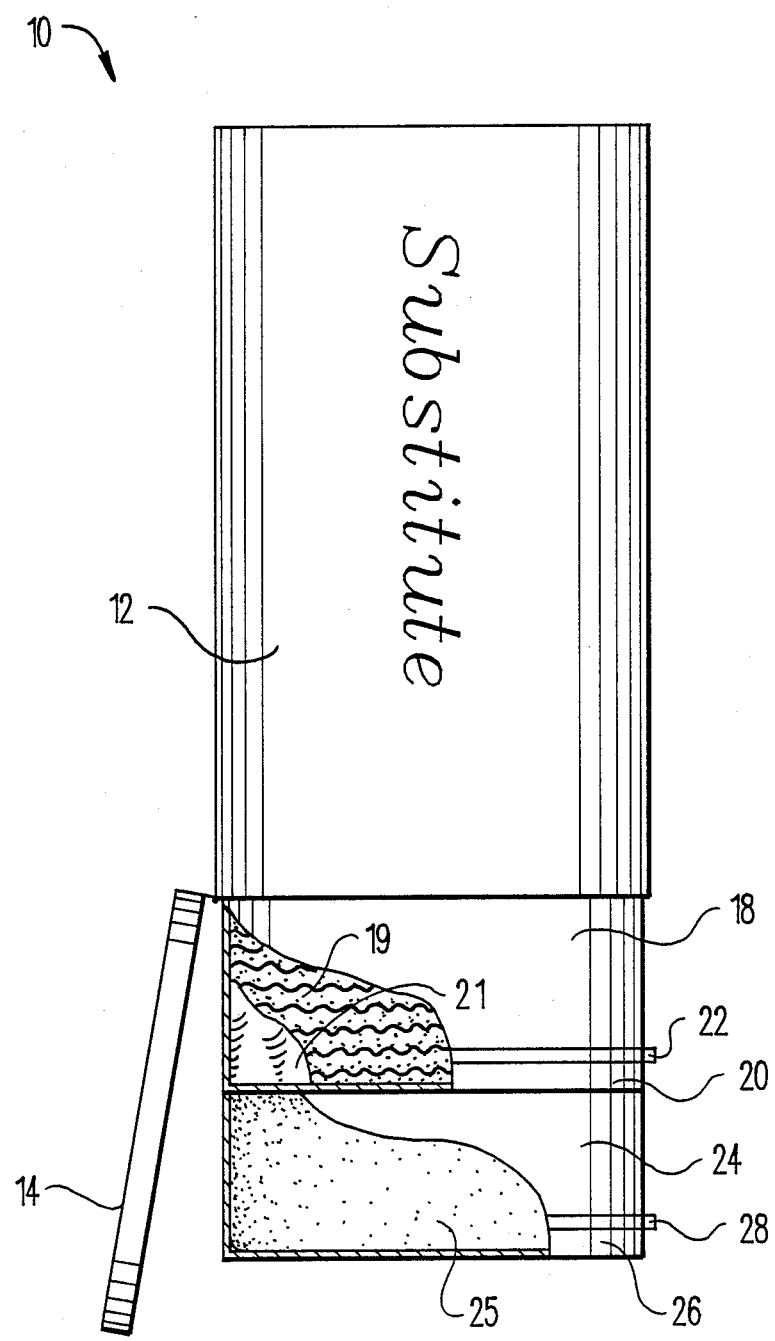
FIG. 3 is a plan view, partially cut away, illustrating the constructional details of the cleaning implement of the present invention.

As illustrated in FIG. 3, the sponge 19 has a front absorbent surface including a dense array of wave form ridges. This provides a slightly abrasive surface which facilitates a preliminary cleaning operation. As previously described, the back surface of the sponge 19 is covered by a soft water proof film 21 such that an individual's hand is maintained out of contact with the absorbent surface of the sponge 19. The irregular wave form surface of the sponge 19 may be formed utilizing a complementary configured roller during the manufacturing process. The second sponge 25 is utilized for a secondary cleaning operation and may be treated with sterilized water so that sensitive and allergic individuals need not utilize a possibly contaminated tap water supply.

Figure 4:
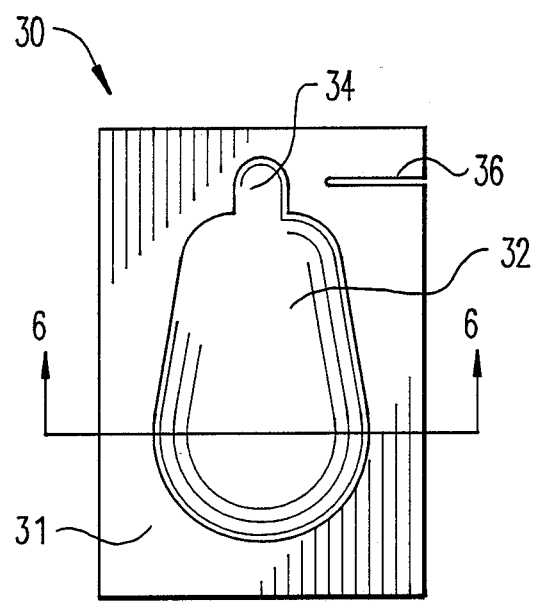
FIG. 4 is a plan view illustrating a disposable packet containing a quantity of mild soap or fragrance.

FIG. 4 illustrates a disposable packet 30 which may be conventionally formed from a plastic material which includes a neck portion 34 adapted for severing by an individual propagating the tear slot 36 across the neck 34. The central bubble portion 32 of the packet 30 may contain a mild hand soap or fragrance or freshening agent, and the packet 30 may be included in the outer package 12.

Figure 5:
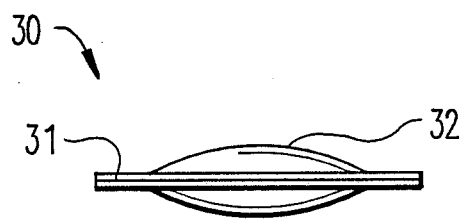
FIG. 5 is an end view of the disposable packet of FIG. 4.

FIG. 5 illustrates an end view of the disposable packet 30.

Figure 6:
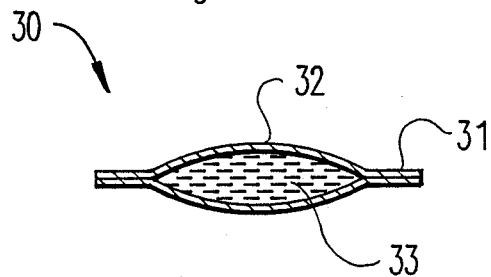
FIG. 6 is a cross sectional view, taken along line 6—6 of FIG. 4.

FIG. 6 illustrates a cross sectional view, taken along line 6—6 of FIG. 4 which illustrates the fluid contents 33.

As may now be understood, the present invention provides an easily portable, disposable, integrated feminine hygiene cleaning system which may be utilized to provide an additional feeling of freshness by women remote from their home environment.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A cleaning implement, comprising:
   an outer package formed from a water proof material;
   a first packet in said outer package formed from a water proof material;
   a first sponge in said first packet, said first sponge having a first absorbent surface having an irregular surface formed by a dense array of continuous, transversely extending, longitudinally evenly spaced wave form ridges and a second water proof surface formed by a thin soft flexible plastic film;
   said first sponge treated with sterilized water and a mild soap;
   a second packet in said outer package formed from a water proof material;
   a second sponge in said second packet, said second sponge treated with sterilized water and a subtle fragrance;
   said first and second packets disposed in overlying relation within said outer package; and
   said first and second packets and said outer package each having a removable cap portion secured by an encircling tear strip.

2. The cleaning implement of claim 1, wherein said sponges are formed from a synthetic material.

3. The cleaning implement of claim 1, wherein said sponges are formed from absorbent paper.

* * * * *